United States Patent
Braun et al.

(10) Patent No.: US 9,309,342 B2
(45) Date of Patent: Apr. 12, 2016

(54) SILICONE ACRYLATE AND TRIFLUOROETHYL METHACRYLATE POLYMER, PREPARATION AND USE THEREOF IN COSMETICS

(71) Applicants: Olivier Braun, St Just St Rambert (FR); Paul Mallo, Croissy-sur-Seine (FR)

(72) Inventors: Olivier Braun, St Just St Rambert (FR); Paul Mallo, Croissy-sur-Seine (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 85 days.

(21) Appl. No.: 14/381,730

(22) PCT Filed: Feb. 15, 2013

(86) PCT No.: PCT/FR2013/050319
§ 371 (c)(1),
(2) Date: Aug. 28, 2014

(87) PCT Pub. No.: WO2013/128095
PCT Pub. Date: Sep. 6, 2013

(65) Prior Publication Data
US 2015/0017114 A1    Jan. 15, 2015

(30) Foreign Application Priority Data
Feb. 29, 2012   (FR) ...................... 12 51848

(51) Int. Cl.
| | |
|---|---|
| *C08F 220/58* | (2006.01) |
| *A61K 8/897* | (2006.01) |
| *A61Q 19/00* | (2006.01) |
| *C08F 220/22* | (2006.01) |
| *C08F 220/38* | (2006.01) |
| *C08F 222/24* | (2006.01) |
| *C08F 230/08* | (2006.01) |
| *C08F 283/12* | (2006.01) |
| *A61K 8/34* | (2006.01) |
| *A61K 8/81* | (2006.01) |

(52) U.S. Cl.
CPC ............ *C08F 220/58* (2013.01); *A61K 8/345* (2013.01); *A61K 8/8135* (2013.01); *A61K 8/897* (2013.01); *A61Q 19/00* (2013.01); *C08F 220/22* (2013.01); *C08F 220/38* (2013.01); *C08F 222/24* (2013.01); *C08F 230/08* (2013.01); *C08F 283/124* (2013.01); *A61K 2800/10* (2013.01); *A61K 2800/34* (2013.01); *A61K 2800/48* (2013.01); *A61K 2800/52* (2013.01); *C08F 2220/585* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Harold et al. | |
| 4,743,667 A * | 5/1988 | Mizutani | ............... C08F 230/08 526/245 |
| 5,368,850 A | 11/1994 | Cauwet et al. | |
| 5,373,044 A | 12/1994 | Adams et al. | |
| 5,458,881 A | 10/1995 | Berger et al. | |
| 5,549,681 A | 8/1996 | Segmuller et al. | |
| 5,670,471 A | 9/1997 | Amalric et al. | |
| 5,888,482 A | 3/1999 | Amalric et al. | |
| 5,958,431 A | 9/1999 | Brancq et al. | |
| 6,437,068 B2 | 8/2002 | Loffler et al. | |
| 6,645,476 B1 | 11/2003 | Morschhauser et al. | |
| 2011/0123933 A1 | 5/2011 | Yun et al. | |

FOREIGN PATENT DOCUMENTS

| | | |
|---|---|---|
| DE | 195 23 596 A1 | 1/1997 |
| EP | 0 301 532 A2 | 2/1989 |
| EP | 0 412 771 A1 | 2/1991 |
| EP | 0 603 019 A1 | 6/1994 |
| EP | 0 684 024 A2 | 11/1995 |
| EP | 0 816 403 A2 | 1/1998 |
| EP | 1 069 142 A1 | 1/2001 |
| EP | 1 116 733 A1 | 7/2001 |
| FR | 2 734 496 A1 | 11/1996 |

(Continued)

OTHER PUBLICATIONS

International Search Report, dated Apr. 22, 2013, from corresponding PCT application.
FR Search Report, dated Jul. 11, 2012, from corresponding FR application.

*Primary Examiner* — Jennifer Berrios
(74) *Attorney, Agent, or Firm* — Young & Thompson

(57) ABSTRACT

An anionic polyelectrolyte resulting from the polymerization, for 100% by mass of: a) a mass ratio ≥70% and ≤98.5% of monomeric units from a monomer with a strong acid function; b) a mass ratio ≥0.5% and ≤10%, —either of a monomer of formula (1a) : R—$(CH_2)3$-$Si(CH_2)2$-$[0$-$Si(CH_3)2$-$]_n$O—$Si(CH_3)_2$—$(CH_2)_3$—R (1a), wherein R represents the monovalent radical: -(0-CH2-CH2-)x[0-$CH_2$—CH(CH3)-]yO—C(═0)-CH═$CH_2$;—or (Ib): $Si(CH_3)_3$-[0-$Si(CH_3)2$-]m[0-$Si(CH_3)$][$(CH_2)_3$—R]—$]_p$O—$Si(CH_2)_3$ (Ib), c) a mass ratio ≥1% and ≤20% of a monomer of formula (II) : $CH_2$═CH(R1)-C(═0)-0-$(CH_2)$n-$CF_3$ (II), formula (I) wherein radical Ri represents a hydrogen atom or a methyl radical, and n is equal to 1, 2 or 3; d) optionally a mass ratio >0% and ≤5% of monomeric units from a monomer of formula (III): $R_2$—C(═0)-0-[($CH_2$—CH($R_4$)-0]m-$R_3$ (III), e) optionally a mass ratio >0% and ≤5% of a cross-linking monomer, method for its preparation and use as a thickener in topical compositions.

14 Claims, No Drawings

(56) References Cited

FOREIGN PATENT DOCUMENTS

| WO | 92/06778 A1 | 4/1992 |
| WO | 92/21316 A1 | 12/1992 |
| WO | 92/21318 A1 | 12/1992 |
| WO | 93/07856 A1 | 4/1993 |
| WO | 93/08204 A1 | 4/1993 |
| WO | 94/27561 A1 | 12/1994 |
| WO | 95/04592 A1 | 2/1995 |
| WO | 95/13863 A1 | 5/1995 |
| WO | 96/37285 A1 | 11/1996 |
| WO | 98/09611 A1 | 3/1998 |
| WO | 98/22207 A1 | 5/1998 |
| WO | 98/47610 A1 | 10/1998 |
| WO | 02/40603 A2 | 5/2002 |

* cited by examiner

SILICONE ACRYLATE AND TRIFLUOROETHYL METHACRYLATE POLYMER, PREPARATION AND USE THEREOF IN COSMETICS

A subject matter of the invention is novel thickening agents and their use in cosmetics and in pharmaceuticals.

It is well known to thicken aqueous phases intended for cosmetic, dermopharmaceutical or pharmaceutical applications by introducing therein synthetic or natural hydrophilic polymers. Natural polymers, such as xanthan or guar gums, are fairly widely used but exhibit the conventional disadvantages of natural products (fluctuating quality and price). For this reason, synthetic thickening polymers are widely used to increase the viscosity of creams, emulsions and various topical solutions. They are provided either in the powder form or in the liquid form. According to the latter option, the polymer is prepared by inverse emulsion polymerization using surfactants and the resulting liquid form is a water-in-oil emulsion comprising the polymer, which emulsion is commonly known as inverse latex.

The thickening polymers in the powder form, the most well known are the polymers based on acrylic acid or the copolymers based on acrylic acid and its esters, such as the polymers sold under the Carbopol™ and Pemulen™ names and which are described in particular in the United States patents U.S. Pat. Nos. 5,373,044 and 2,798,053 and also in the European patent EP 0 301 532, or also such as the homopolymers or copolymers based on 2-acrylamido-2-methylpropanesulfonic acid sold under the Aristoflex™ name and which are described in particular in the European patents EP 0 816 403, EP 1 116 733 and EP 1 069 142. These polymer powders are obtained by precipitating polymerization in an organic solvent, such as benzene, ethyl acetate, cyclohexane or tert-butanol.

The inverse latexes, such as those sold under the names Sepigel™ 305, Simulgel™ 600, Simulgel™ EG, Simulgel™ EPG, Simulgel™ NS, Simulgel™ INS 100, Simulgel™ A, Sepiplus™ 400, Sepiplus™ 250, Sepiplus™ 265 and Sepiplus™ S, obtained by inverse emulsion polymerization can be more easily handled and disperse very rapidly in water. They develop remarkably high thickening performances which are probably the consequence of the process for their preparation, a dispersed-phase polymerization reaction, which results in polymers of very high molecular weights.

The abovementioned polymers are essentially intended to thicken aqueous phases of cosmetic, dermopharmaceutical or pharmaceutical topical formulations.

In point of fact, some of the formulations, more particularly those intended for the care of the skin, also comprise relatively high amounts of glycerol, typically between 5% and 10% by weight, in order to increase their moisturizing potential. However, as the presence of glycerol within them also considerably increases their sticky effect, preparers add silicone oils thereto in order to limit or eliminate this sticky effect.

However, the addition of silicone oils complicates the preparation of these formulations. Furthermore, the presence of silicone oils in formulations which are intended to be in direct contact with the skin is badly received by the final consumer. The cosmetics industry is thus attempting to limit the use of them.

The inventors have thus attempted to develop novel thickening polymers which are effective over a broad pH range and which are capable of reducing or eliminating the sticky effect brought about by the presence of glycerol, without it being necessary to add a third compound, such as silicone derivatives. They have found that the powders of polymers resulting from the precipitating polymerization of fluoromonomers and of monomers having a strong acid functional group solve these problems.

For this reason, according to a first aspect, a subject matter of the invention is a linear, branched or crosslinked anionic polyelectrolyte resulting from the polymerization, for 100% by weight:

a) of a proportion by weight of greater than or equal to 70% and less than or equal to 98.5% of monomer units resulting from a monomer comprising a strong acid functional group which is free or partially or completely salified;

b) of a proportion by weight of greater than or equal to 0.5% and less than or equal to 10%,
either of a monomer of formula (Ia):

(Ia), in which:
R represents the monovalent radical:

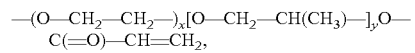

in which x and y represent, independently of one another, an integer of greater than or equal to 0 and less than or equal to 40, it being understood that the sum x+y is greater than 0 and less than 50; and n represents an integer of greater than or equal to 0 and less than or equal to 45, said monomer of formula (Ia) having a molecular weight of greater than or equal to 1500 and less than or equal to 7000;

or of a monomer of formula (Ib):

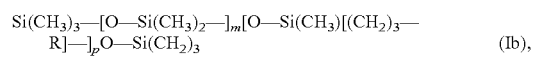

(Ib), in which:
R represents a monovalent radical of formula:

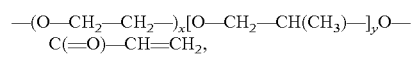

in which x and y represent, independently of one another, an integer of greater than or equal to 0 and less than or equal to 40, it being understood that the sum x+y is greater than 0 and less than 50;

m represents an integer of greater than or equal to 1 and less than or equal to 7, and p represents, independently of m, an integer of greater than or equal to 1 and less than 20;

said monomer of formula (Ib) having a molecular weight of greater than or equal to 1000 and less than or equal to 4000;

c) of a proportion by weight of greater than or equal to 1% and less than or equal to 20% of a monomer of formula (II):

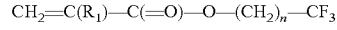

in which formula (I) the $R_1$ radical represents a hydrogen atom or a methyl radical and n represents an integer equal to 1, 2 or 3;

d) optionally of a proportion by weight of greater than 0% and less than or equal to 5% of monomer units resulting from a monomer of formula (III):

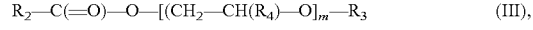

(III), in which formula (II) m represents a number greater than or equal to 0 and less than or equal to 50, $R_2$ represents an unsaturated monovalent aliphatic radical comprising from 2 to 4 carbon atoms, $R_4$ represents a hydrogen atom, a methyl radical or an ethyl radical and $R_3$ represents a saturated or unsaturated, linear or branched, aliphatic hydrocarbon radical comprising from 8 to 30 carbon atoms, and e) optionally of a proportion by weight of greater than 0% and less than or equal to 5% of at least one diethylenic or polyethylenic crosslinking monomer.

The term "branched polyelectrolyte" denotes a nonlinear polyelectrolyte which has pendant chains, so as to obtain, when it is dissolved in water, a high state of entanglement resulting in very high viscosities at low rate gradient.

The term "crosslinked polyelectrolyte" denotes a nonlinear polyelectrolyte which is provided in the form of a three-dimensional network which is insoluble in water but which can expand in water and which thus results in the achievement of a chemical gel.

The polyelectrolyte obtained by the process according to the invention can comprise crosslinked units and/or branched units.

According to a specific aspect of the present invention, in the formula (II) as defined above, n is equal to 1.

According to another specific aspect of the present invention, in the formula (II) as defined above, $R_1$ represents a methyl radical.

The term "monomer comprising a strong acid functional group which is free or partially or completely salified" denotes in particular the monomers having a sulfonic ($-SO_3H$) functional group.

According to a specific aspect, said monomer comprising a strong acid functional group which is free or partially or completely salified is free, partially salified or completely salified 2-methyl-2-[(1-oxo-2-propenyl)amino]-1-propanesulfonic acid.

The term "partially or completely salified strong acid functional group" denotes, in the context of the present invention, an acid functional group which is partially or completely salified, in particular in the form of an alkali metal salt, such as, for example, the sodium salt or the potassium salt, or in the form of an ammonium salt.

According to another specific aspect, a subject matter of the invention is an anionic polyelectrolyte as defined above in which said at least one monomer comprising a partially or completely salified strong acid functional group is 2-methyl-2-[(1-oxo-2-propenyl)amino]-1-propanesulfonic acid partially or completely salified in the ammonium salt form.

According to another specific aspect, the linear, branched or crosslinked polyelectrolyte is characterized in that the proportion by weight of monomer units resulting from the monomer comprising a strong acid functional group which is free or partially or completely salified is less than or equal to 95%.

In the formula (III) as defined above, the divalent radical:

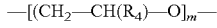

represents in particular:
either a chain composed solely of ethoxyl groups ($R_4$=H; n>0),
or a chain composed solely of propoxyl groups ($R_4$=CH_3; n>0).
or a chain composed solely of butoxyl groups ($R_4$=$C_2H_5$; n>0),
or a chain composed of at least two different groups chosen from the ethoxyl, propoxyl and/or butoxyl groups.

When this chain is composed of different groups, they are distributed all along this chain, sequentially or randomly.

The term "saturated or unsaturated, linear aliphatic hydrocarbon radical comprising from 8 to 30 carbon atoms" denotes more particularly for $R_3$, in the formula (II) as defined above:
either a radical derived from linear primary alcohols, such as, for example, those derived from octyl, pelargonic, decyl, undecyl, undecenyl, lauryl, tridecyl, myristyl, pentadecyl, cetyl, heptadecyl, stearyl, oleyl, linoleyl, nonadecyl, arachidyl, behenyl, erucyl or l-triacontyl alcohol. They are then the octyl, nonyl, decyl, undecyl, 10-undecenyl, dodecyl, tridecyl, tetradecyl, pentadecyl, hexadecyl, heptadecyl, octadecyl, 9-octadecenyl, 10,12-octadeca-dienyl, 13-docosenyl or triacontanyl radicals;
or a radical derived from Guerbet alcohols, which are branched 1-alkanols corresponding to the general formula:

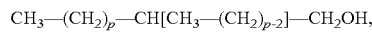

in which p represents an integer of between 2 and 14, such as, for example, the 2-ethylhexyl, 2-propylheptyl, 2-butyloctyl, 2-pentylnonyl, 2-hexyldecyl or 2-octyl-dodecyl radical;
or a radical derived from the isoalkanols corresponding to the general formula:

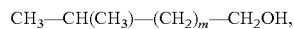

in which m represents an integer of between 2 and 26, such as, for example, the 4-methylpentyl, 5-methyl-hexyl, 6-methylheptyl, 15-methylpentadecyl or 16-methylheptadecyl radical;
or the 2-hexyloctyl, 2-octyldecyl or 2-hexyl-dodecyl radical.

The term "saturated or unsaturated, linear or branched, aliphatic hydrocarbon radical comprising from 8 to 30 carbon atoms" more particularly denotes for $R_3$ in the formula (III) as defined above, an alkyl radical comprising from 12 to 22 carbon atoms.

In the formula (III) as defined above, m more particularly represents a number greater than or equal to 0 or less than or equal to 25.

In the formula (III) as defined above, $R_2$ more particularly represents the vinyl ($CH_2$=CH—) radical or the isopropenyl [$CH_2$=C(CH_3)—] radical.

According to a more specific aspect of the present invention, said monomer of formula (III) as defined above is chosen from:
pentacosaethoxylated behenyl methacrylate, the compound of formula (III) as defined above in which $R_3$ represents the docosanyl radical, $R_2$ represents the isopropenyl radical, $R_4$ represents a hydrogen atom and n is equal to 25;
tetraethoxylated lauryl acrylate, which compound corresponds to the formula (III) as defined above in which $R_3$ represents the dodecyl radical, $R_2$ represents the vinyl radical, $R_4$ represents a hydrogen atom and n is equal to 4,
eicosaethoxylated stearyl methacrylate, the compound of formula (III) as defined above in which $R_3$ represents the stearyl radical, $R_2$ represents the isopropenyl radical, $R_4$ represents a hydrogen atom and n is equal to 20,
tetraethoxylated lauryl methacrylate, which compound corresponds to the formula (III) as defined above in which $R_3$ represents the dodecyl radical, $R_2$ represents the isopropenyl radical, $R_4$ represents a hydrogen atom and n is equal to 4, or
stearyl methacrylate, the compound of formula (III) as defined above in which $R_3$ represents the stearyl radical, $R_2$ represents the isopropenyl radical, $R_4$ represents a hydrogen atom and n is equal to 0.

According to a more specific aspect of the present invention, said monomer of formula (Ia) as defined above is Silmer™ ACR Di-50, sold by Siltech, with a molecular weight equal to 4100 and referenced in Chemical Abstracts under the registry number RN=128754-61-6.

According to a more specific aspect of the present invention, said monomer of formula (Ia) as defined above is Silmer™ ACR Di-10, sold by Siltech, with a molecular weight equal to 1100.

According to a more specific aspect of the present invention, said monomer of formula (Ib) as defined above is Silmer™ ACR D208, sold by Siltech, with a molecular weight equal to 3000 and referenced in Chemical Abstracts under the registry number RN=518299-28-0.

According to a more specific aspect of the present invention, said monomer of formula (Ib) as defined above is Silmer™ ACR D2, sold by Siltech, with a molecular weight equal to 1400 and referenced in Chemical Abstracts under the registry number RN=158061-40-6.

According to a specific aspect, a subject matter of the invention is more particularly a polyelectrolyte as defined above resulting from the polymerization, for 100% by weight:
  a) of a proportion by weight of greater than or equal to 75% and less than or equal to 90% of monomer units resulting from a monomer comprising a strong acid functional group which is free or partially or completely salified;
  b) of a proportion by weight of greater than or equal to 1% and less than or equal to 10% of monomer units resulting from a monomer of formula (Ia) as defined above or from a monomer of formula (Ib) as defined above;
  c) of a proportion by weight of greater than or equal to 5% and less than or equal to 20% of monomer units resulting from 2,2,2-trifluoroethyl methacrylate; and
  d) optionally of a proportion by weight of greater than 0% and less than or equal to 5% of monomer units resulting from the compound of formula (III) as defined above.

According to another specific aspect of the present invention, the polyelectrolyte as defined above is crosslinked.

According to the latter aspect, said at least one diethylenic or polyethylenic crosslinking monomer is chosen in particular from diallyloxyacetic acid or one of the salts, such as its sodium salt, triallylamine, trimethylolpropane triacrylate, ethylene glycol dimethacrylate, diethylene glycol diacrylate, diallylurea or methylenebis(acrylamide), or a mixture of several of these compounds.

According to a very specific aspect of the present invention, the crosslinking agent employed is methylenebis(acrylamide) or trimethylolpropane triacrylate (TMPTA).

The crosslinking agent is then generally employed in the proportion by weight, expressed with respect to the monomers employed, of 0.005% by weight to 5% by weight and more particularly of 0.5% by weight to 2.5% by weight.

According to a specific aspect, a subject matter of the invention is more particularly a polyelectrolyte as defined above resulting from the polymerization, for 100% by weight:
  a) of a proportion by weight of greater than or equal to 75% and less than or equal to 85% of monomer units resulting from a monomer comprising a strong acid functional group which is free or partially or completely salified;
  b) of a proportion by weight of greater than or equal to 1% and less than or equal to 10% of monomer units resulting from a monomer of formula (Ia) as defined above or from a monomer of formula (Ib) as defined above;
  c) of a proportion by weight of greater than or equal to 5% and less than or equal to 20% of monomer units resulting from 2,2,2-trifluoroethyl methacrylate; and
  e) of a proportion by weight of greater than 0% and less than or equal to 5% by weight of monomer units resulting from at least one diethylenic or polyethylenic crosslinking monomer.

Another subject matter of the invention is a process for the preparation of the polyelectrolyte as defined above, characterized in that it comprises:
  a stage a) of preparation of a reaction mixture comprising, in the desired molar proportions and in a solvent (S), the monomer or monomers comprising a strong acid functional group which is free or partially or completely salified, the monomer of formula (Ia) or the monomer of formula (Ib) the monomer of formula (II); if necessary or if desired, the monomer units resulting from the compound of formula (III); and, if necessary or if desired, the diethylenic or polyethylenic crosslinking monomer or monomers, said solvent (S) being:
  either a ketone of formula (IV):

in which R3 and R4, which are identical or different, represent, independently of one another, a methyl radical, an ethyl radical, an isopropyl radical or an isobutyl radical;
  or a mixture consisting of, for 100 mol %:
    water in a proportion of greater than 0 mol % and less than or equal to 25 mol %; and
    a ketone of formula (IV) as defined above in a proportion of greater than or equal to 75 mol % and less than 100%;
  or tert-butanol;
  a stage b) during which the polymerization reaction is initiated by introduction, into said reaction mixture prepared in stage a), of a free radical initiator and is then allowed to take place until its conclusion, in order to obtain a precipitate of said polyelectrolyte.

According to another specific aspect of the present invention, in stage b) of the process as defined above, the polymerization reaction is initiated at a temperature equal to or greater than 50° C. using a radical initiator which produces radicals by homolysis, such as dilauroyl peroxide, azobis(isobutyronitrile) or also azo derivatives.

According to another specific aspect of the present invention, in stage b) of the process as defined above, the polymerization reaction is initiated by a redox pair, such as a redox pair which generates hydrogensulfite ($HSO_3$) ions, such as the cumene hydroperoxide/sodium metabisulfite ($Na_2S_2O_5$) pair or the cumene hydroperoxide/thionyl chloride ($SOCl_2$) pair, at a temperature of less than or equal to 20° C., if desired accompanied by a polymerization coinitiator, such as, for example, azobis(isobutyronitrile), dilauroyl peroxide or sodium persulfate, and then carried out quasiadiabatically.

The process as defined above can additionally comprise:
  a stage c) of isolation of said precipitate obtained in stage b) by separation from said solvent (S) and then, if necessary or if desired,
  a stage d) of drying said precipitate resulting from stage c).

According to another specific aspect of the present invention, in stage c) of the process as defined above, the separation of the precipitate obtained from said organic solvent is carried out by filtration.

According to another specific aspect, a subject matter of the invention is a process as defined above in which said solvent(s) is:
either acetone, or a water/acetone mixture in a water/acetone molar ratio of greater than 0 and less than or equal to 5/95, or tert-butanol.

Another subject matter of the invention is the use of the anionic polyelectrolyte as defined above as thickener and/or as stabilizer and/or as emulsifier for a cosmetic, dermopharmaceutical or pharmaceutical topical composition.

A topical composition according to the invention, intended to be applied to the skin or mucous membranes of man or animals, can be composed of a topical emulsion comprising at least one aqueous phase and at least one oil phase. This topical emulsion can be of the oil-in-water (O/W), water-in-oil (W/O), oil-in-water-in-oil (O/W/O) or water-in-oil-in-water (W/O/W) type. The oil phase of the topical emulsion can be composed of a mixture of one or more oils.

A topical composition according to the invention can be intended for a cosmetic use or can be used to prepare a medicament intended for the treatment of diseases of the skin, scalp and mucous membranes. In the latter case, the topical composition then comprises an active principle which can, for example, be an anti-inflammatory agent, a muscle relaxant, an antifungal, an antibacterial or an antidandruff agent.

When the topical composition is used as cosmetic composition intended to be applied to the skin, to the scalp or to the mucous membranes, it may or may not comprise an active principle, for example a moisturizing agent, a tanning agent, a sunscreen, an antiwrinkle agent, an agent having a slimming purpose, an agent for combating free radicals, an antiacne agent, an antifungal or an antidandruff agent.

The topical composition according to the invention normally comprises between 0.1% and 10% by weight and more particularly from 1% to 5% by weight of the anionic polyelectrolyte as defined above.

According to a specific aspect, the topical composition as defined above additionally comprises from 1% by weight to 10% by weight of glycerol.

The pH of the topical composition is preferably greater than or equal to 3.

The topical composition can additionally comprise compounds conventionally included in compositions of this type, for example fragrances, preservatives, dyes, pigments, sunscreens, active ingredients, emollients or surfactants.

The anionic polyelectrolyte according to the invention is an advantageous substitute for the inverse latexes sold under the names of Sepigel™ 305, Sepigel™ 501, Simulgel™ EG, Simulgel™ EPG, Simulgel™ NS, Simulgel™ INS 100, Simulgel™ 600, Simulgel™ A, Sepiplus™ 265, Sepiplus™ 250, Sepiplus™ 400 or Sepiplus™ S by the Applicant Company as it also exhibits good compatibility with the other excipients used in the preparation of formulations such as milks, lotions, creams, soaps, baths, balms, shampoos or conditioners. It can also be employed with said Sepigel™ and/or Simulgel™ and/or Sepiplus™ products.

It is in particular compatible with the concentrates described and claimed in the international publications WO 92/06778, WO 95/04592, WO 95/13863, WO 96/37285, WO 98/22207 or WO 98/47610 or in FR 2 734 496, with the surfactants described in WO 93/08204. It is particularly compatible with Montanov™ 68, Montanov™ 82, Montanov™ 202, Montanov™ L, Montanov™ S, Fluidanov™ 20X or Easynov™.

It can also be used to form aqueous gels at acidic pH which are cosmetically or physiologically acceptable, such as those described in WO 93/07856; it can also be used in combination with nonionic celluloses to form, for example, styling gels, such as those described in EP 0 684 024, or also in combination with esters of fatty acids and of sugar to form compositions for the treatment of the hair or skin, such as those described in EP 0 603 019, or also in shampoos or conditioners, such as described and claimed in WO 92/21316, or, finally, in combination with an anionic homopolymer, such as Carbopol™, to form hair treatment products, such as those described in DE 19523596.

It is also compatible with N-acylated derivatives of amino acids, which allows it to be used in soothing compositions, in particular for sensitive skin, such as those described or claimed in WO 92/21318, WO 94/27561 or WO 98/09611. It is also compatible with thickening and/or gelling polymers, such as hydrocolloids of vegetable or biosynthetic origin, for example xanthan gum, gum karaya, carrageenates, alginates or galacto-mannans; such as silicates; such as cellulose and its derivatives; such as starch and its hydrophilic derivatives; or such as polyurethanes.

The anionic polyelectrolyte according to the invention in addition makes it possible to dispense with the use of silicone oil in topical compositions comprising glycerol, in that it inhibits the sticky effect brought about by this trial.

For this reason, according to a final aspect, a subject matter of the invention is a topical composition comprising between 0.1% and 10% by weight and more particularly from 1% to 5% by weight of the anionic polyelectrolyte as defined above and from 1% by weight to 10% by weight of glycerol and characterized in that it is devoid of silicone oil.

The following examples illustrate the invention without, however, limiting it.

EXAMPLE 1

Preparation of an ATBS/TRIFEMA/ACR-D2 Copolymer Crosslinked with TMPTA 67.7 g of 2-methyl-2-[(1-oxo-2-propenyl)amino]-1-propanesulfonic acid (ATBS) are charged to a reactor maintained at 25° C. with stirring and containing 487.5 g of tert-butanol and then ammonia is added thereto until a pH value of approximately 6 is achieved. After a time sufficient to achieve good homogenization of the solution, the latter is deoxygenated by sparging with nitrogen and then 13.8 g of 2,2,2-trifluoroethyl methacrylate (TRIFEMA), 4.3 g of Silmer™ ACR D2 (compound of formula (Ib), identified under the Chemical Abstract number RN=158061-40-6, with a molecular weight equal to 1400), 12.5 g of deionized water and 2 g of trimethylolpropane triacrylate (TMPTA) are added.

The reaction mixture is left stirring for sixty minutes; it is then heated until the temperature of 60° C. is reached. 1 g of dilauroyl peroxide is then added thereto. The reaction medium is subsequently again left stirring for approximately 60 minutes, then brought to 80° C. and left at this temperature for sixty minutes. An additional 0.33 g of dilauroyl peroxide is added and the medium is kept stirred at 80° C. for two hours.

After cooling, the powder which is formed during polymerization is filtered off and dried in order to obtain the desired product, subsequently known as: Polyelectrolyte 1.

Evaluation of the Thickening Power

Viscosity (μ) of an aqueous dispersion comprising 2% by weight of Polyelectrolyte 1 [Brookfield RVT, Spindle 6, Rate: 5 revolutions/minute (S6, R5)]: μ=102 000 mPa·s.

Viscosity (μ) of an aqueous dispersion comprising 2% by weight of Polyelectrolyte 1 and 1% by weight of sodium chloride [Brookfield RVT (S6, R5)]: μ=2900 mPa·s.

Evaluation of the Sticky Nature of Aqueous Gels Comprising Glycerol 250 g of an aqueous gel are prepared by mixing 2.5 g of Polyelectrolyte 1, 25 g of glycerol and 222.5 g of water.

As basis for comparison, 250 g of an aqueous gel are prepared by mixing 6.25 g of Sepigel™ 305, 25 g of glycerol and 218.75 g of water.

On spreading each of the two gels over a different surface of the back of the hand, the absence of sticky effect was observed for the gel comprising Polyelectrolyte 1 according to the invention, contrary to the gel according to the state of the art.

EXAMPLE 2

Preparation of an ATBS/TRIFEMA/ACR-D2/SMA Copolymer Crosslinked with TMPTA

The operation is carried out in the same way as in example 1 but using 2.6 g of Silmer™ ACR D2 and reducing the TMPTA content to 1.2 g. 1.4 g of stearyl methacrylate (SMA) are also added to the reaction medium before polymerization. Polyelectrolyte 2 is obtained.

Evaluation of the Thickening Power

Viscosity (μ) of an aqueous dispersion comprising 1% by weight of Polyelectrolyte 2 [Brookfield RVT (S6, R5)]: μ=67 600 mPa·s.

Viscosity (μ) of an aqueous dispersion comprising 1% by weight of Polyelectrolyte 2 and 1% by weight of sodium chloride [Brookfield RVT (S6, R5)]: μ=12 660 mPa·s.

Evaluation of the Sticky Nature of Aqueous Gels Comprising Glycerol 250 g of an aqueous gel are prepared by mixing 2.5 g of Polyelectrolyte 2, 25 g of glycerol and 222.5 g of water.

On spreading each gel over the back of the hand, the absence of sticky effect is observed for the gel comprising Polyelectrolyte 2 according to the invention.

EXAMPLE 3

Preparation of an ATBS/TRIFEMA/ACR-Di-50/SMA Copolymer Crosslinked with TMPTA

The operation is carried out in the same way as in example 2 but using 2.6 g of Silmer™ ACR Di-50 (compound of formula (Ia), identified under the Chemical Abstract number RN=128754-61-0, with a molecular weight equal to 4100) in place of Silmer™ ACR D2. Polyelectrolyte 3 is obtained.

Evaluation of the Thickening Power

Viscosity (μ) of an aqueous dispersion comprising 1% by weight of Polyelectrolyte 3 [Brookfield RVT (S6, R5)]: μ=39 200 mPa·s.

Viscosity (μ) of an aqueous dispersion comprising 1% by weight of Polyelectrolyte 3 and 1% by weight of sodium chloride [Brookfield RVT (S6, R5)]: μ=10 940 mPa·s.

Evaluation of the Sticky Nature of Aqueous Gels Comprising Glycerol 250 g of an aqueous gel are prepared by mixing 2.5 g of Polyelectrolyte 3, 25 g of glycerol and 222.5 g of water.

On spreading each gel over the back of the hand, the absence of sticky effect is observed for the gel comprising Polyelectrolyte 3 according to the invention.

EXAMPLE 4

Preparation of an ATBS/TRIFEMA/ACR-D2 Copolymer

The operation is carried out in the same way as in example 1 but using 7.1 g of Silmer™ ACR D2 and removing the TMPTA. Polyelectrolyte 4 is obtained.

Evaluation of the Thickening Power

Viscosity (μ) of an aqueous dispersion comprising 1% by weight of Polyelectrolyte 4 [Brookfield RVT (S6, R5)]: μ=45 000 mPa·s.

Viscosity (μ) of an aqueous dispersion comprising 1% by weight of Polyelectrolyte 4 and 1% by weight of sodium chloride [Brookfield RVT (S6, R5)]: μ=2820 mPa·s.

Evaluation of the Sticky Nature of Aqueous Gels Comprising Glycerol 250 g of an aqueous gel are prepared by mixing 2.5 g of Polyelectrolyte 4, 25 g of glycerol and 222.5 g of water.

On spreading each gel over the back of the hand, the absence of sticky effect is observed for the gel comprising Polyelectrolyte 4 according to the invention.

Examples of Formulations Comprising Glycerol and Devoid of Silicone Oils Prepared with Polyelectrolytes According to the Invention

EXAMPLE 5

Make-up-removing Emulsion Comprising Sweet Almond Oil

| | |
|---|---|
| Montanov ™ 68: | 5% |
| Sweet almond oil: | 5% |
| Water: | q.s. for 100% |
| Polyelectrolyte 1: | 0.3% |
| Glycerol: | 5% |
| Preservative: | 0.2% |
| Fragrance: | 0.3% |

EXAMPLE 6

Emulsion for Atopy-Prone Skin

| | |
|---|---|
| Arlacel ™ P135: | 2.00% |
| Polyelectrolyte 1: | 1.00% |
| Lanol ™ 1688: | 14.00% |
| Primol ™ 352: | 8.00% |
| Glycerol: | 5.00% |
| Water: | q.s. for 100% |
| Magnesium sulfate: | 0.70% |
| Sepicide ™ HB: | 0.30% |
| Sepicide ™ CI: | 0.20% |
| Micropearl ™ M310: | 5.00% |

The definitions of the commercial products used in the examples are as follows:

Montanov™ 68 (cetearyl glucoside) is a self-emulsifiable composition as described in WO 92/06778, sold by SEPPIC.

Arlacel™ P135 is a mixture of glycerol monostearate, glycerol distearate and polyoxyethylene glycerol stearate, sold by Croda.

Sepicide™ CI, imidazolidinyl urea, is a preservative, sold by SEPPIC.

Lanol™ 1688 is an emollient ester having a nongreasy effect, sold by SEPPIC.

Sepicide™ HB, which is a mixture of phenoxyethanol, methylparaben, ethylparaben, propylparaben and butylparaben, is a preservative, sold by SEPPIC.

Micropearl™ 310 is an ultrafine powder with a very soft feel and with a mattifying action, sold by Matsumo.

Primol™ 352 is a mineral oil, sold by Exxon.

The invention claimed is:

1. A linear, branched or crosslinked anionic polyelectrolyte resulting from the polymerization, for 100% by weight:
   a) of a proportion by weight of greater than or equal to 70% and less than or equal to 98.5% of monomer units resulting from a monomer comprising a strong acid functional group which is free or partially or completely salified;
   b) of a proportion by weight of greater than or equal to 0.5% and less than or equal to 10%,
   either of a monomer of formula (Ia):

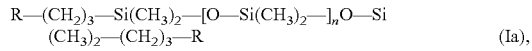

in which:
   R represents the monovalent radical:

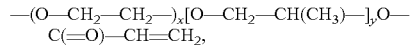

in which x and y represent, independently of one another, an integer of greater than or equal to 0 and less than or equal to 40, it being understood that the sum x+y is greater than 0 and less than 50; and
   n represents an integer of greater than or equal to 0 and less than or equal to 45,
   said monomer of formula (Ia) having a molecular weight of greater than or equal to 1500 and less than or equal to 7000;
   or of a monomer of formula (Ib):

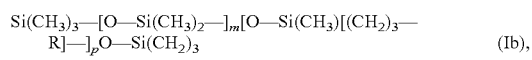

in which:
   R represents a monovalent radical of formula:

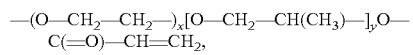

in which x and y represent, independently of one another, an integer of greater than or equal to 0 and less than or equal to 40, it being understood that the sum x+y is greater than 0 and less than 50;
   m represents an integer of greater than or equal to 1 and less than or equal to 7, and
   p represents, independently of m, an integer of greater than or equal to 1 and less than 20;
   said monomer of formula (Ib) having a molecular weight of greater than or equal to 1000 and less than or equal to 4000;
   c) of a proportion by weight of greater than or equal to 1% and less than or equal to 20% of a monomer of formula (II):

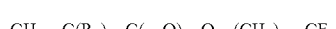

in which formula (I) the $R_1$ radical represents a hydrogen atom or a methyl radical and n represents an integer equal to 1, 2 or 3;

d) optionally of a proportion by weight of greater than 0% and less than or equal to 5% of monomer units resulting from a monomer of formula (III):

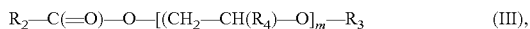

in which formula (II) m represents a number greater than or equal to 0 and less than or equal to 50, $R_2$ represents an unsaturated monovalent aliphatic radical comprising from 2 to 4 carbon atoms, $R_4$ represents a hydrogen atom, a methyl radical or an ethyl radical and $R_3$ represents a saturated or unsaturated, linear or branched, aliphatic hydrocarbon radical comprising from 8 to 30 carbon atoms, and
   e) optionally of a proportion by weight of greater than 0% and less than or equal to 5% of at least one diethylenic or polyethylenic crosslinking monomer.

2. The anionic polyelectrolyte as defined in claim 1, for which, in the formula (II), n is equal to 1.

3. The anionic polyelectrolyte as defined in claim 1, for which, in the formula (II), $R_1$ represents a methyl radical.

4. The anionic polyelectrolyte as defined in claim 1, for which said monomer comprising a strong acid functional group which is free or partially or completely salified is 2-methyl-2-[(1-oxo-2-propenyl)amino]-1-propanesulfonic acid which is free, partially salified or completely salified in the sodium salt or potassium salt form or in the ammonium salt form.

5. The anionic polyelectrolyte as defined in claim 1, for which said monomer of formula (III) is chosen from pentacosaethoxylated behenyl methacrylate, tetraethoxylated lauryl acrylate, eicosaethoxylated stearyl methacrylate, tetraethoxylated lauryl methacrylate or stearyl methacrylate.

6. The anionic polyelectrolyte as defined in claim 1 resulting from the polymerization, for 100% by weight:
   a) of a proportion by weight of greater than or equal to 75% and less than or equal to 90% of monomer units resulting from a monomer comprising a strong acid functional group which is free or partially or completely salified;
   b) of a proportion by weight of greater than or equal to 1% and less than or equal to 10% of monomer units resulting from a monomer of formula (Ia) or from a monomer of formula (Ib);
   c) of a proportion by weight of greater than or equal to 5% and less than or equal to 20% of monomer units resulting from 2,2,2-trifluoroethyl methacrylate; and
   d) optionally of a proportion by weight of greater than 0% and less than or equal to 5% of monomer units resulting from the compound of formula (III) as defined above.

7. The anionic polyelectrolyte as defined in claim 1, characterized in that it is crosslinked.

8. The anionic polyelectrolyte as defined in claim 7, characterized in that said at least one diethylenic or polyethylenic crosslinking monomer is chosen from methylenebis(acrylamide) or trimethylolpropane triacrylate.

9. The polyelectrolyte as defined in claim 7 resulting from the polymerization, for 100% by weight:
   a) of a proportion by weight of greater than or equal to 75% and less than or equal to 85% of monomer units resulting from a monomer comprising a strong acid functional group which is free or partially or completely salified;
   b) of a proportion by weight of greater than or equal to 1% and less than or equal to 10% of monomer units resulting from a monomer of formula (Ia) or from a monomer of formula (Ib);
   c) of a proportion by weight of greater than or equal to 5% and less than or equal to 20% of monomer units resulting from 2,2,2-trifluoroethyl methacrylate; and e) of a proportion by weight of greater than 0% and less than or equal to 5% by weight of monomer units resulting from at least one diethylenic or polyethylenic crosslinking monomer.

10. A process for the preparation of the polyelectrolyte as defined in claim 1, characterized in that it comprises:

a stage a) of preparation of a reaction mixture comprising, in the desired molar proportions and in a solvent (S), the monomer or monomers comprising a strong acid functional group which is free or partially or completely salified, the monomer of formula (Ia) or monomer of formula (Ib), the monomer of formula (II); if necessary or if desired, the monomer units resulting from the compound of formula (III); and, if necessary or if desired, the diethylenic or polyethylenic crosslinking monomer or monomers, said solvent (S) being:

either a ketone of formula (IV):

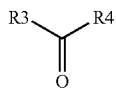
(IV)

in which R3 and R4, which are identical or different, represent, independently of one another, a methyl radical, an ethyl radical, an isopropyl radical or an isobutyl radical;

or a mixture consisting of, for 100 mol %:
water in a proportion of greater than 0 mol % and less than or equal to 25 mol %; and
a ketone of formula (IV) as defined above in a proportion of greater than or equal to 75 mol % and less than 100%;
or tert-butanol;

a stage b) during which the polymerization reaction is initiated by introduction, into said reaction mixture prepared in stage a), of a free radical initiator and is then allowed to take place until its conclusion, in order to obtain a precipitate of said polyelectrolyte, if necessary or if desired, a stage c) of isolation of said precipitate obtained in stage b) by separation from said solvent (S) and then, if necessary or if desired, a stage d) of drying said precipitate resulting from stage c).

11. Method of using the anionic polyelectrolyte as defined in claim 1 as thickener and/or as stabilizer and/or as emulsifier for a cosmetic, dermopharmaceutical or pharmaceutical topical composition.

12. A topical cosmetic composition, characterized in that it comprises from 1% to 5% by weight of the anionic polyelectrolyte as defined in claim 1 and from 1% by weight to 10% by weight of glycerol.

13. The composition as defined in claim 12, characterized in that it is devoid of silicone oil.

14. The anionic polyelectrolyte as defined in claim 2, for which, in the formula (II), $R_1$ represents a methyl radical.

* * * * *